(12) United States Patent
Zhao et al.

(10) Patent No.: US 12,053,231 B2
(45) Date of Patent: Aug. 6, 2024

(54) SYSTEMS AND METHODS FOR CONTROLLING DELIVERY OF ELECTROSURGICAL ENERGY

(71) Applicant: Covidien LP, Mansfield, MA (US)

(72) Inventors: Jing Zhao, Superior, CO (US); Robert H. Wham, Boulder, CO (US); Christopher T. Brown, Bolder, CO (US); Anjali Dhiman, Commerce City, CO (US)

(73) Assignee: COVIDIEN LP, Mansfield, MA (US)

( * ) Notice: Subject to any disclaimer, the term of this patent is extended or adjusted under 35 U.S.C. 154(b) by 697 days.

(21) Appl. No.: 17/027,855

(22) Filed: Sep. 22, 2020

(65) Prior Publication Data

US 2021/0100606 A1 Apr. 8, 2021

Related U.S. Application Data

(60) Provisional application No. 62/909,361, filed on Oct. 2, 2019.

(51) Int. Cl.
*A61B 18/14* (2006.01)
*G06N 3/047* (2023.01)
(Continued)

(52) U.S. Cl.
CPC ......... *A61B 18/1445* (2013.01); *G06N 3/047* (2023.01); *G06N 3/08* (2013.01);
(Continued)

(58) Field of Classification Search
CPC ...... A61B 18/1445; A61B 2018/00672; A61B 2018/00678
See application file for complete search history.

(56) References Cited

U.S. PATENT DOCUMENTS 5,558,671 A 9/1996 Yates
6,454,781 B1 9/2002 Witt et al.
(Continued)

FOREIGN PATENT DOCUMENTS

EP 2836145 A1 2/2015
WO 2014140085 A1 9/2014

OTHER PUBLICATIONS

Extended European Search Report dated Feb. 17, 2021 corresponding to counterpart Patent Application EP 20199765.7.
(Continued)

*Primary Examiner* — Sean W Collins
*Assistant Examiner* — Ryan T Clark
(74) *Attorney, Agent, or Firm* — Carter, DeLuca & Farrell LLP

(57) ABSTRACT

A computer-implemented method for controlling delivery of electrosurgical energy to a vessel to seal the vessel, includes collecting data from an electrosurgical system including an instrument and energy source while the instrument is delivering electrosurgical energy from the energy source to a vessel, predicting by using a machine learning algorithm a burst pressure probability of the vessel based on the data, and determining if the vessel is adequately sealed based on the prediction. The data includes an electrical parameter associated with the delivery of the electrosurgical energy. In a case where it is determined that the vessel is not adequately sealed: determining an output by a second machine learning algorithm, communicating the determined output to a computing device associated with the energy source for use in formulating an energy-delivery algorithm, and delivering, using the instrument, additional electrosurgical from the energy source to the vessel to seal the vessel according to the energy-delivery algorithm.

16 Claims, 11 Drawing Sheets

(51) Int. Cl.
*G06N 3/08* (2023.01)
*A61B 18/00* (2006.01)

(52) U.S. Cl.
CPC .............. *A61B 2018/00404* (2013.01); *A61B 2018/0063* (2013.01); *A61B 2018/00672* (2013.01); *A61B 2018/00678* (2013.01); *A61B 2018/00714* (2013.01); *A61B 2018/00755* (2013.01); *A61B 2018/00773* (2013.01)

(56) References Cited

U.S. PATENT DOCUMENTS

| | | | |
|---|---|---|---|
| 7,720,267 B2 | 5/2010 | Fuchs et al. | |
| 8,034,049 B2 | 10/2011 | Odom et al. | |
| 8,058,771 B2 | 11/2011 | Giordano et al. | |
| 8,253,303 B2 | 8/2012 | Giordano et al. | |
| 8,512,365 B2 | 8/2013 | Wiener et al. | |
| 8,779,648 B2 | 7/2014 | Giordano et al. | |
| 8,831,327 B2 | 9/2014 | Santamaria-Pang et al. | |
| 8,864,761 B2 | 10/2014 | Johnson | |
| 9,017,326 B2 | 4/2015 | DiNardo et al. | |
| 9,039,695 B2 | 5/2015 | Giordano et al. | |
| 9,060,776 B2 | 6/2015 | Yates et al. | |
| 9,237,921 B2 | 1/2016 | Messerly et al. | |
| 9,445,832 B2 | 9/2016 | Wiener et al. | |
| 9,724,118 B2 | 8/2017 | Schulte et al. | |
| 10,194,972 B2 | 2/2019 | Yates et al. | |
| 10,376,305 B2 | 8/2019 | Yates et al. | |
| 10,420,579 B2 | 9/2019 | Wiener et al. | |
| 10,786,298 B2 | 9/2020 | Johnson | |
| 2002/0072686 A1 | 6/2002 | Hoey | |
| 2006/0036372 A1 | 2/2006 | Yener et al. | |
| 2007/0173803 A1 | 7/2007 | Wham et al. | |
| 2007/0173805 A1 | 7/2007 | Weinberg et al. | |
| 2007/0276245 A1 | 11/2007 | Konofagou | |
| 2008/0281316 A1 | 11/2008 | Carlton et al. | |
| 2009/0298703 A1 | 12/2009 | Gough et al. | |
| 2011/0071521 A1 | 3/2011 | Gilbert | |
| 2011/0118736 A1* | 5/2011 | Harper | A61B 5/4869 606/51 |
| 2012/0283731 A1 | 11/2012 | Unger et al. | |
| 2013/0285758 A1 | 10/2013 | Aldridge et al. | |
| 2013/0296908 A1* | 11/2013 | Schulte | A61B 17/320068 606/169 |
| 2016/0331455 A1* | 11/2016 | Hancock | A61B 18/1815 |
| 2017/0000422 A1* | 1/2017 | Moturu | A61B 5/0022 |
| 2017/0000553 A1 | 1/2017 | Wiener et al. | |
| 2017/0007308 A1 | 1/2017 | Mun | |
| 2018/0235686 A1 | 8/2018 | Sahakian et al. | |
| 2018/0338788 A1 | 11/2018 | Harper et al. | |
| 2019/0021783 A1 | 1/2019 | Asher et al. | |
| 2019/0201038 A1 | 7/2019 | Yates et al. | |
| 2019/0201042 A1 | 7/2019 | Nott et al. | |
| 2019/0201044 A1 | 7/2019 | Shelton, IV et al. | |
| 2019/0274662 A1 | 9/2019 | Rockman et al. | |
| 2021/0104311 A1* | 4/2021 | Schulman | G16H 50/30 |

OTHER PUBLICATIONS

European Examination Report for Application No. 20199765.7 dated Aug. 22, 2023, 4 pages.

\* cited by examiner

SYSTEMS AND METHODS FOR CONTROLLING DELIVERY OF ELECTROSURGICAL ENERGY

CROSS-REFERENCE TO RELATED APPLICATIONS

This application claims the benefit of and priority to U.S. Provisional Patent Application Ser. No. 62/909,361 filed Oct. 2, 2019, the entire disclosure of which is incorporated by reference herein.

BACKGROUND

Technical Field

The disclosure relates to predicting vessel parameters and, more particularly, to systems and methods incorporating machine learning-based prediction of vessel parameters to control the delivery of electrosurgical energy from surgical devices based on the estimated vessel parameters.

Background of Related Art

Surgical instruments are utilized to perform various functions on tissue structures. A surgical forceps, for example, is a plier-like device which relies on mechanical action between its jaws to grasp, clamp, and constrict tissue. Energy-based surgical forceps utilize both mechanical clamping action and energy to treat, e.g., coagulate, cauterize, and/or seal, a vessel.

Surgical instruments such as energy-based surgical forceps are effective at treating tissue, typically without tissue temperature feedback. For example, with respect to energy-based surgical forceps, vessel sealing is accomplished by subjecting a vessel to a controlled energy profile under a controlled pressure.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the disclosure, a computer-implemented method for controlling delivery of electrosurgical energy to a vessel to seal the vessel is presented. The computer-implemented method includes collecting data from an electrosurgical system including an instrument and energy source while the instrument is delivering electrosurgical energy from the energy source to a vessel to seal the vessel. The method further includes communicating the data to a machine learning algorithm, predicting a burst pressure probability of the vessel by the machine learning algorithm, and determining if the vessel is adequately sealed based on the prediction. The data includes an electrical parameter associated with the delivery of the electrosurgical energy. In a case where it is determined that the vessel is not adequately sealed, the method further includes determining an output based upon the data by a second machine learning algorithm, communicating the determined output to a computing device associated with the energy source for use in formulating an energy-delivery algorithm, and delivering, using the instrument, additional electrosurgical energy from the energy source to the vessel to seal the vessel according to the energy-delivery algorithm.

In an aspect of the present disclosure, the machine learning algorithm may include a neural network.

In another aspect of the present disclosure, the neural network may include a feed-forward network, a convolutional network, and/or a recurrent network.

In an aspect of the present disclosure, the method may further include training the neural network based on one or more of measuring sensor data or identifying patterns in data.

In yet another aspect of the present disclosure, the method may further include training the neural network based on training data including impedance, vessel temperature, vessel mass, vessel surface area, accumulated energy, and/or burst pressure probability.

In a further aspect of the present disclosure, the training may include supervised learning, unsupervised learning and/or reinforcement learning.

In an aspect of the present disclosure, the reinforcement learning may include a reward based on a burst pressure probability value and/or an impedance punishment value.

In a further aspect of the present disclosure, the burst pressure probability value may be a scaler. The burst pressure probability value may be determined by, in a case that the vessel temperature is a first temperature range for a first predetermined period of time for protein denaturing, increasing the burst pressure probability value by a first amount. In a case that the vessel temperature is a second temperature range for a second predetermined period of time for a predetermined percentage of water to be removed, the burst pressure probability value may be determined by increasing the burst pressure probability value by a second amount. In a case that the vessel temperature is a third temperature range for a third predetermined period of time for allowing thermoset gelatin to congeal and jaws to cool, the burst pressure probability value may be determined by increasing the burst pressure probability value by a third amount.

In yet another aspect of the present disclosure, the impedance punishment value may be a second scaler. The impedance punishment value may be determined by, in a case that impedance of the vessel is greater than a first impedance threshold, setting the impedance punishment value to −1. In a case where the impedance of the vessel is less than the first impedance threshold, the impedance punishment value may be determined by setting the impedance punishment value to 0.

In a further aspect of the present disclosure, the method may further include, in a case where it is determined that the vessel is adequately sealed, ceasing delivery of the electrosurgical energy and/or the additional electrosurgical energy.

In accordance with aspects of the disclosure, a system for controlling electrosurgical energy is presented. The system includes an electrosurgical system, including an instrument and energy source, one or more processors, and memory coupled to the one or more processors. The memory having instructions stored thereon which, when executed by the one or more processors, cause the system to: collect data from the electrosurgical system while the instrument is delivering electrosurgical energy from the energy source to a vessel to seal the vessel, the data including an electrical parameter associated with the delivery of the electrosurgical energy, communicate the data to a machine learning algorithm, predict, by the machine learning algorithm, a burst pressure probability of the vessel, and determine if the vessel is adequately sealed based on the prediction. In a case where it is determined that the vessel is not adequately sealed, the instructions, when executed, further cause the system to determine, by a second machine learning algorithm, an output based upon the data, communicate the determined output to a computing device associated with the energy source for use in formulating an energy-delivery algorithm, and deliver, using the instrument, additional electrosurgical energy from the energy source to the vessel to seal the vessel according to the energy-delivery algorithm.

In yet a further aspect of the present disclosure, the machine learning algorithm may include a neural network.

In yet another aspect of the present disclosure, the neural network may include a feed-forward network, a convolutional network, or a recurrent network.

In a further aspect of the present disclosure, the instructions, when executed, may further cause the system to train the neural network based on one or more of measuring sensor data and/or identifying patterns in data.

In yet a further aspect of the present disclosure, the instructions, when executed may further cause the system to train the neural network based on training data including impedance, vessel temperature, vessel mass, vessel surface area, accumulated energy, and/or burst pressure probability.

In yet another aspect of the present disclosure, the training may include supervised learning, unsupervised learning and/or reinforcement learning.

In a further aspect of the present disclosure, the reinforcement learning may include a reward based on a burst pressure probability value and/or an impedance punishment value.

In a further aspect of the present disclosure, the burst pressure probability value is between 0 and 1. The burst pressure probability value may be determined by: in a case that the vessel temperature is a first temperature range for a first predetermined period of time for protein denaturing, increasing the burst pressure probability value by a first amount. In a case that the vessel temperature is a second temperature range for a second predetermined period of time for a predetermined percentage of water to be removed, the burst pressure probability value may be determined by increasing the burst pressure probability value by a second amount. In a case that the vessel temperature is a third temperature range for a third predetermined period of time for allowing thermoset gelatin to congeal and jaws to cool, the burst pressure probability value may be determined by increasing the burst pressure probability value by a third amount.

In yet another aspect of the present disclosure, the reward further may include the impedance punishment value is between −1 and 0. The impedance punishment value may be determined by: in a case that impedance of the vessel is greater than a first impedance threshold, setting the impedance punishment value to −1. In a case where the impedance of the vessel is less than the first impedance threshold, the impedance punishment value may be determined by setting the impedance punishment value to 0.

In an aspect of the present disclosure, in a case where it is determined that the vessel is adequately sealed, the instructions, when executed, may further cause the system to cease delivery of the electrosurgical energy or the additional electrosurgical energy.

In accordance with aspects of the disclosure, a non-transitory storage medium that stores a program causing a computer to execute a computer-implemented method for controlling delivery of electrosurgical energy to a vessel to seal the vessel. The computer-implemented method includes collecting data from an electrosurgical system including an instrument and energy source while the instrument is delivering electrosurgical energy from the energy source to a vessel to seal the vessel The method further includes communicating the data to a machine learning algorithm, predicting, by the machine learning algorithm, a burst pressure probability of the vessel, and determining if the vessel is adequately sealed based on the prediction. In a case where it is determined that the vessel is not adequately sealed, the method further includes determining, by a second machine learning algorithm, an output based upon the data, communicating the determined output to a computing device associated with the energy source for use in formulating an energy-delivery algorithm, and delivering, using the instrument, additional electrosurgical from the energy source to the vessel to seal the vessel. The data includes an electrical parameter associated with the delivery of the electrosurgical energy according to the energy-delivery algorithm.

BRIEF DESCRIPTION OF THE DRAWINGS

Various aspects and features of the disclosure are described herein with reference to the drawings wherein.

DETAILED DESCRIPTION

Tissue sealing involves heating tissue to liquefy the collagen and elastin in the tissue so that it reforms into a fused mass with significantly-reduced demarcation between the opposing tissue structures. To achieve a tissue seal without causing unwanted damage to tissue at the surgical site or collateral damage to adjacent tissue, it is necessary to control the application of energy to tissue, thereby controlling the temperature of tissue during the sealing process. To properly seal tissue, a balance must be sustained during the sealing process between sufficient heating to denature proteins and vaporize fluids and unwanted/collateral damage.

With respect to utilizing vessel burst pressure probability information in real-time in order to control the application of energy to tissue to achieve a tissue seal, it would be desirable to determine burst pressure probability during the tissue sealing process. As detailed below, this may be accomplished by utilizing data already available from the electrosurgical system and running a machine learning algorithm to estimate burst pressure probability based upon that data. The estimated burst pressure probability may then be fed back to the controller for use in controlling the application of energy to tissue in accordance therewith. Burst pressure probability, as utilized herein, is the probability that a sealed vessel will not burst under a threshold fluid pressure provided through the vessel. For example, a burst pressure probability indicating an adequately sealed vessel may be a 95% probability of a burst pressure greater than 360 mmHg, although other suitable probabilities and/or pressures are also contemplated.

The systems and methods of the disclosure detailed below may be incorporated into any type of surgical system for treating tissue such as, for example, the electrosurgical systems detailed hereinbelow. For purposes of illustration and in no way limiting the scope of the appended claims, the systems and methods for estimating burst pressure probability for use in controlling application of electrosurgical energy to tissue are described in the disclosure in the context of electrosurgical systems.

Figure 1A:
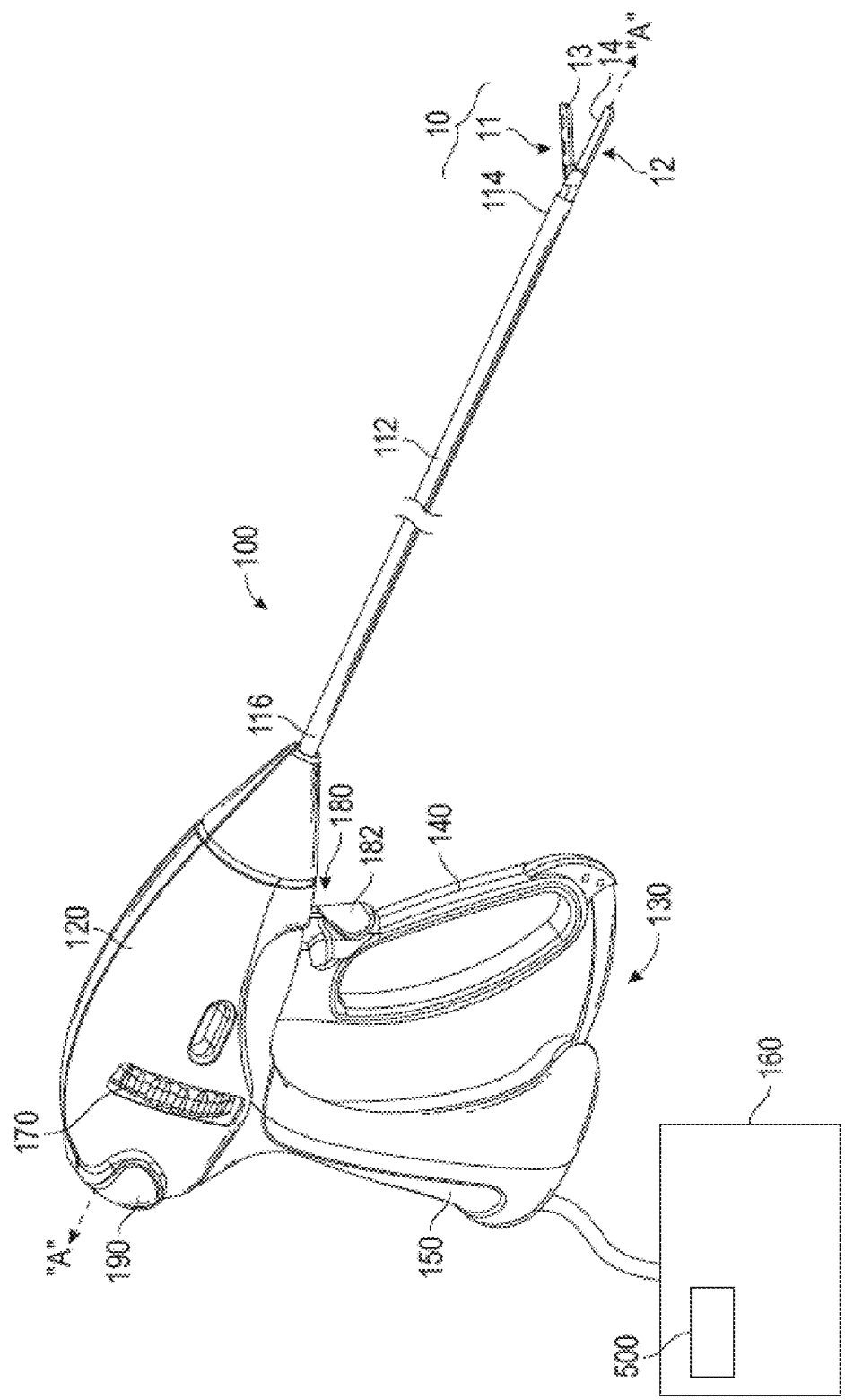
FIG. 1A is a perspective view of a surgical system provided in accordance with the disclosure including an energy-based surgical instrument and a generator.
Figure 1B:
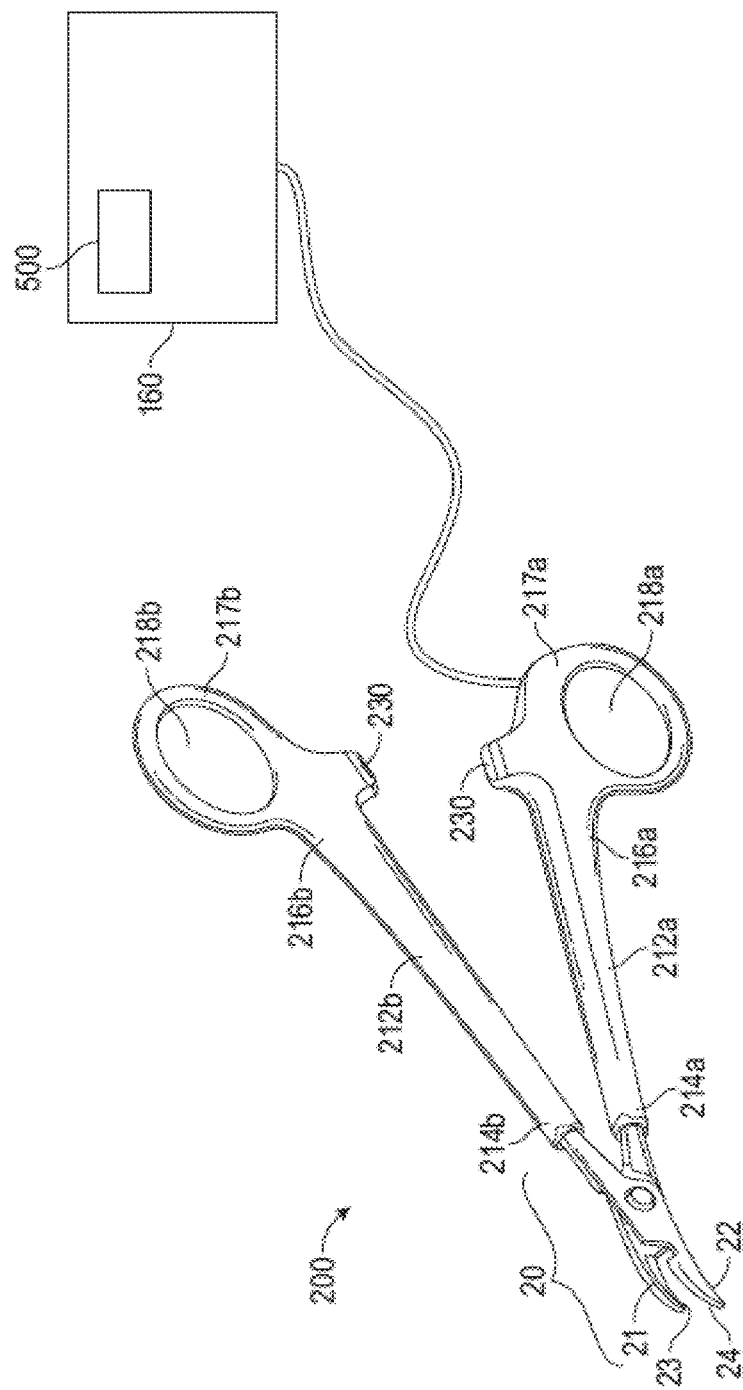
FIG. 1B is a perspective view of another surgical system provided in accordance with the disclosure including another energy-based surgical instrument and the generator.

Referring now to FIGS. 1A and 1B, FIG. 1A depicts an electrosurgical system including a shaft-based surgical forceps 100 and an electrosurgical generator 160 for use therewith, and FIG. 1B depicts an electrosurgical system including a hemostat-style surgical forceps 200 and electrosurgical generator 160 for use therewith. For the purposes herein, either forceps 100, forceps 200, or any other suitable surgical instrument and/or system may be utilized in accordance with the disclosure. Obviously, different electrical and mechanical connections and considerations apply to each particular type of instrument and system; however, the aspects and features of the disclosure remain generally consistent regardless of the configuration of the instrument or system used therewith.

Turning now to FIG. 1A, forceps 100 defines a longitudinal axis "A-A" and includes a housing 120, a handle assembly 130, a rotating assembly 170, a trigger assembly 180, and an end effector assembly 10. Forceps 100 further includes a shaft 112 having a distal end 114 configured to mechanically engage end effector assembly 10 and a proximal end 116 that mechanically engages housing 120. Forceps 100 may further include a surgical cable extending therefrom and configured to connect forceps 100 to an electrosurgical generator 160 such that at least one of the electrically-conductive tissue treating surfaces 13, 14 of jaw members 11, 12 of end effector assembly 10 may be energized to treat tissue grasped therebetween, e.g., upon activation of activation switch 190.

With continued reference to FIG. 1A, handle assembly 130 includes fixed handle 150 and a movable handle 140. Fixed handle 150 is integrally associated with housing 120 and handle 140 is movable relative to fixed handle 150. Rotating assembly 170 is rotatable in either direction about a longitudinal axis "A-A" to rotate end effector assembly 10 about longitudinal axis "A-A." Housing 120 houses the internal working components of forceps 100.

End effector assembly 10 is shown attached at distal end 114 of shaft 112 and includes a pair of opposing jaw members 11 and 12. Each of jaw members 11 and 12 includes an electrically-conductive tissue treating surface 13, 14, respectively, configured to grasp tissue therebetween and conduct electrosurgical energy therethrough to treat, e.g., seal, tissue. End effector assembly 10 is designed as a unilateral assembly, i.e., where jaw member 12 is fixed relative to shaft 112 and jaw member 11 is movable relative to shaft 112 and fixed jaw member 12. However, end effector assembly 10 may alternatively be configured as a bilateral assembly, i.e., where both jaw member 11 and jaw member 12 are movable relative to one another and to shaft 112. In some embodiments, a knife assembly (not shown) is disposed within shaft 112, and a knife channel (not shown) is defined within one or both jaw members 11, 12 to permit reciprocation of a knife blade (not shown) therethrough, e.g., upon activation of trigger 182 of trigger assembly 180, to cut tissue disposed between jaw members 11, 12.

Continuing with reference to FIG. 1A, movable handle 140 of handle assembly 130 is ultimately connected to a drive assembly (not shown) that, together, mechanically cooperate to impart movement of jaw members 11 and 12 between a spaced-apart position and an approximated position to grasp tissue between tissue treating surfaces 13 and 14 of jaw members 11, 12, respectively. As shown in FIG. 1A, movable handle 140 is initially spaced-apart from fixed handle 150 and, correspondingly, jaw members 11, 12 are in the spaced-apart position. Movable handle 140 is depressible from this initial position to a depressed position corresponding to the approximated position of jaw members 11, 12.

Referring now to FIG. 1B, forceps 200 is shown including two elongated shafts 212a and 212b, each having a proximal end 216a and 216b, and a distal end 214a and 214b, respectively. Forceps 200 is configured for use with an end effector assembly 20 that is similar to end effector assembly 10 of forceps 100 (see FIG. 1A). More specifically, end effector assembly 20 is attached to distal ends 214a and 214b of shafts 212a and 212b, respectively and includes a pair of opposing jaw members 21 and 22 that are movable relative to one another. Each shaft 212a and 212b includes a handle 217a and 217b disposed at the proximal end 216a and 216b thereof. Each handle 217a and 217b defines a finger hole 218a and 218b therethrough for receiving a finger of the user. As can be appreciated, finger holes 218a and 218b facilitate movement of shafts 212a and 212b relative to one another from an open position, wherein jaw members 21 and 22 are disposed in spaced-apart relation relative to one another, to a closed position, wherein jaw members 21 and 22 cooperate to grasp tissue therebetween.

A ratchet 230 may be included for selectively locking jaw members 21 and 22 of forceps 200 relative to one another at various different positions. It is envisioned that ratchet 230 may include graduations or other visual markings that may enable the user to easily and quickly ascertain and control the amount of closure force desired between the jaw members 21 and 22.

With continued reference to FIG. 1B, one of the shafts may be adapted to receive a surgical cable configured to connect forceps 200 to electrosurgical generator 160. Electrosurgical generator 160, as will be described in greater detail below, provides power to end effector assembly 20 such that at least one of the electrically-conductive tissue treating surfaces 23, 24 of jaw members 21, 22, respectively, of end effector assembly 20 may be energized to treat, e.g., seal, tissue grasped therebetween.

Similar to forceps 100 (FIG. 1A), forceps 200 may further include a knife assembly (not shown) disposed within either of shafts 212a, 212b and a knife channel (not shown) defined within one or both jaw members 21, 22 to permit reciprocation of a knife blade (not shown) therethrough.

Figure 2:
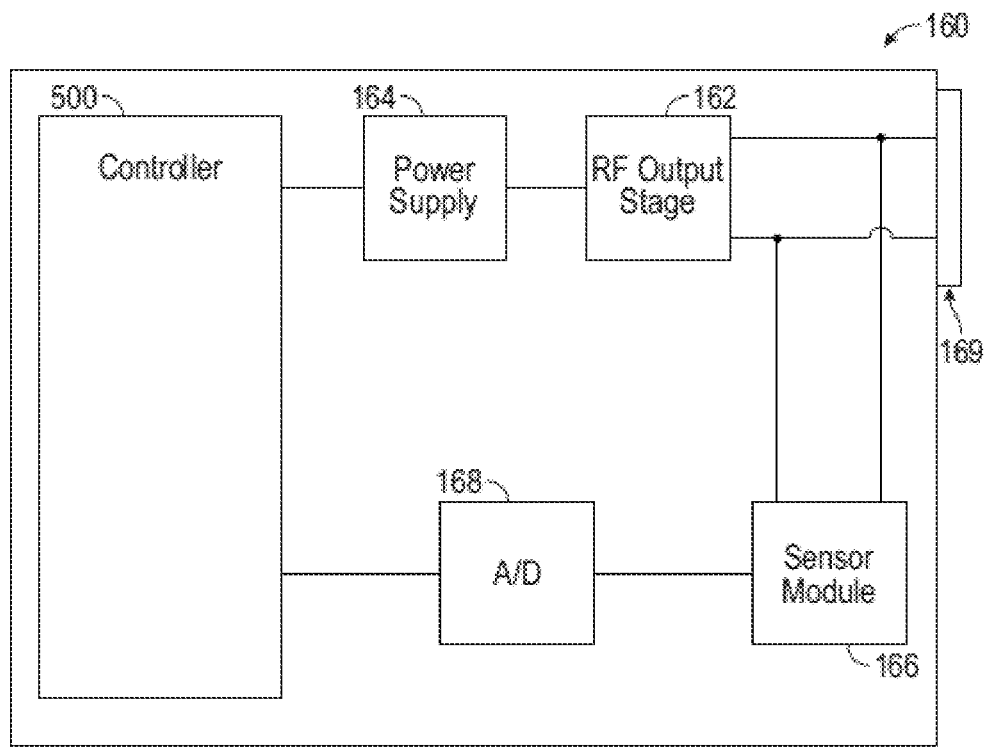
FIG. 2 is a block diagram of the generator of the systems of FIGS. 1A and 1B in accordance with the disclosure.

Referring now to FIG. 2, there is shown a block diagram of exemplary components of electrosurgical generator 160 in accordance with aspects of the disclosure. In the illustrated embodiment, the generator 160 includes a controller 500, a power supply 164, a radio-frequency (RF) energy output stage 162, a sensor module 166, one or more analog-to-digital converters (ADCs) 168, and one or more connector ports 169 that accommodate various types of electrosurgical instruments, e.g., forceps 10 and forceps 200 (FIGS. 1A and 1B, respectively). The generator 160 can include a user interface (not shown), which permits a user to select various parameters for the generator 160, such as mode of operation and power setting. In various embodiments, the power setting can be specified by a user to be between zero and a power limit, such as, for example, five watts, thirty watts, seventy watts, or ninety-five watts.

The electrosurgical generator 160 may be any suitable type of generator to accommodate various types of electrosurgical instruments (e.g., monopolar electrosurgical instrument and bipolar electrosurgical instrument). The electrosurgical generator 160 may also be configured to operate in a variety of modes, such as ablation, cutting, coagulation, and sealing. The electrosurgical generator 160 may include a switching mechanism (e.g., relays) to switch the supply of RF energy among the connectors 169 to which various electrosurgical instruments may be connected. For example, when an electrosurgical instrument, e.g., forceps 100 (FIG. 1A) or forceps 200 (FIG. 1B), is connected to the electrosurgical generator 160, the switching mechanism switches the supply of RF energy to the appropriate plug 169. In embodiments, the electrosurgical generator 160 may be configured to provide RF energy to a plurality of instruments simultaneously.

In various embodiments, the generator 160 may include a sensor module 166, which includes a plurality of sensors, e.g., an RF current sensor, and an RF voltage sensor. Various components of the generator 160, namely, the RF output stage 162 and the RF current and voltage sensors of sensor module 166 may be disposed on a printed circuit board (PCB). The RF current sensor of sensor module 166 may be coupled to the active terminal and provides measurements of the RF current supplied by the RF output stage 162. In embodiments, the RF current sensor of sensor module 166 may be coupled to the return terminal. The RF voltage sensor of sensor module 166 is coupled to the active and return terminals and provides measurements of the RF voltage supplied by the RF output stage 162. In embodiments, the RF current and voltage sensors of sensor module 166 may be coupled to active and return leads, which interconnect the active and return terminals and to the RF output stage 162, respectively.

The RF current and voltage sensors of the sensor module 166 sense and provide the sensed RF voltage and current signals, respectively, to the controller 500 of generator 160, which then may adjust the output of the power supply and/or the RF output stage 162 in response to the sensed RF voltage and current signals. Controller 500 may additionally or alternatively determine power, impedance, and/or other properties based on the sensed RF voltage and current and adjust the output of the power supply and/or the RF output stage 162 in response thereto. Controller 500 is described in greater detail hereinbelow (see FIG. 5).

The sensed voltage and current from sensor module 166 are fed to ADCs 168. The ADCs 168 sample the sensed voltage and current to obtain digital samples of the voltage and current of the RF output stage 162. The digital samples are processed by the controller 500 and used to generate a control signal to control the DC/AC inverter of the RF output stage 162 and the preamplifier. The ADCs 168 communicate the digital samples to the controller 500 for further processing.

Figure 3:
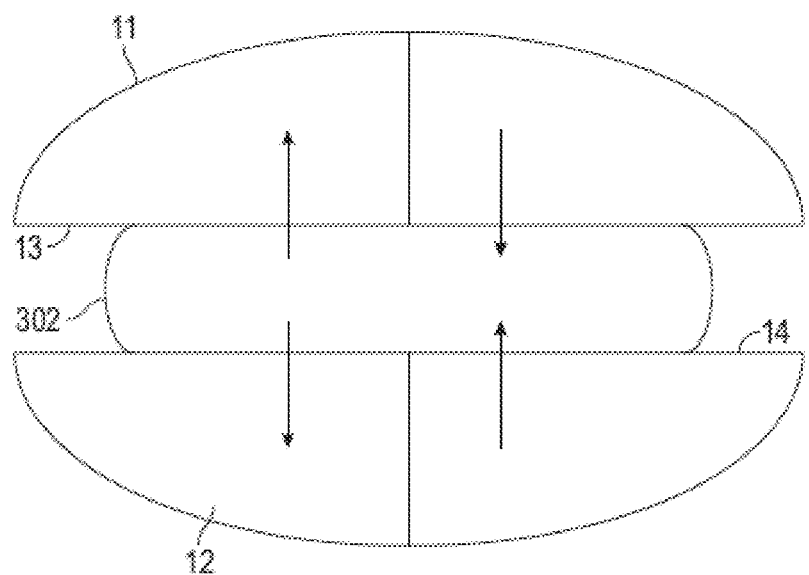
FIG. 3 is a transverse, cross-sectional view of the end effector assembly of the energy-based surgical instrument of the surgical system of FIG. 1A, shown grasping and applying energy to tissue in accordance with the disclosure.

Referring now to FIG. 3, a transverse, cross-sectional view of the end effector assembly 10 of forceps 100 of FIG. 1A is shown. Jaw members 11, 12 grasp tissue 302 between the electrically conductive surfaces 13, 14 of the jaw members 11, 12. Generator 160 (FIG. 2) supplies electrosurgical energy to electrically conductive surfaces 13, 14 at different potentials such that electrosurgical energy is conducted therebetween and through the grasped tissue 302 to heat and thereby treat, e.g., seal, the tissue 302. As noted above, by controlling the application of energy from the generator 160 (FIG. 2) to surfaces 13, 14, and the pressure applied to tissue by surfaces 13, 14, the heating of the tissue 302 can be controlled to achieve a tissue seal. As also noted above, the disclosure provides systems and methods for estimating burst pressure probability for use in controlling the application of energy to the tissue 302 (e.g., a vessel), using available data. This is advantageous in that it provides an estimated burst pressure probability in real-time, which is an indication of the effectiveness of the tissue seal, despite the inability to directly measure burst pressure probability utilizing traditional sensors.

Figure 4:
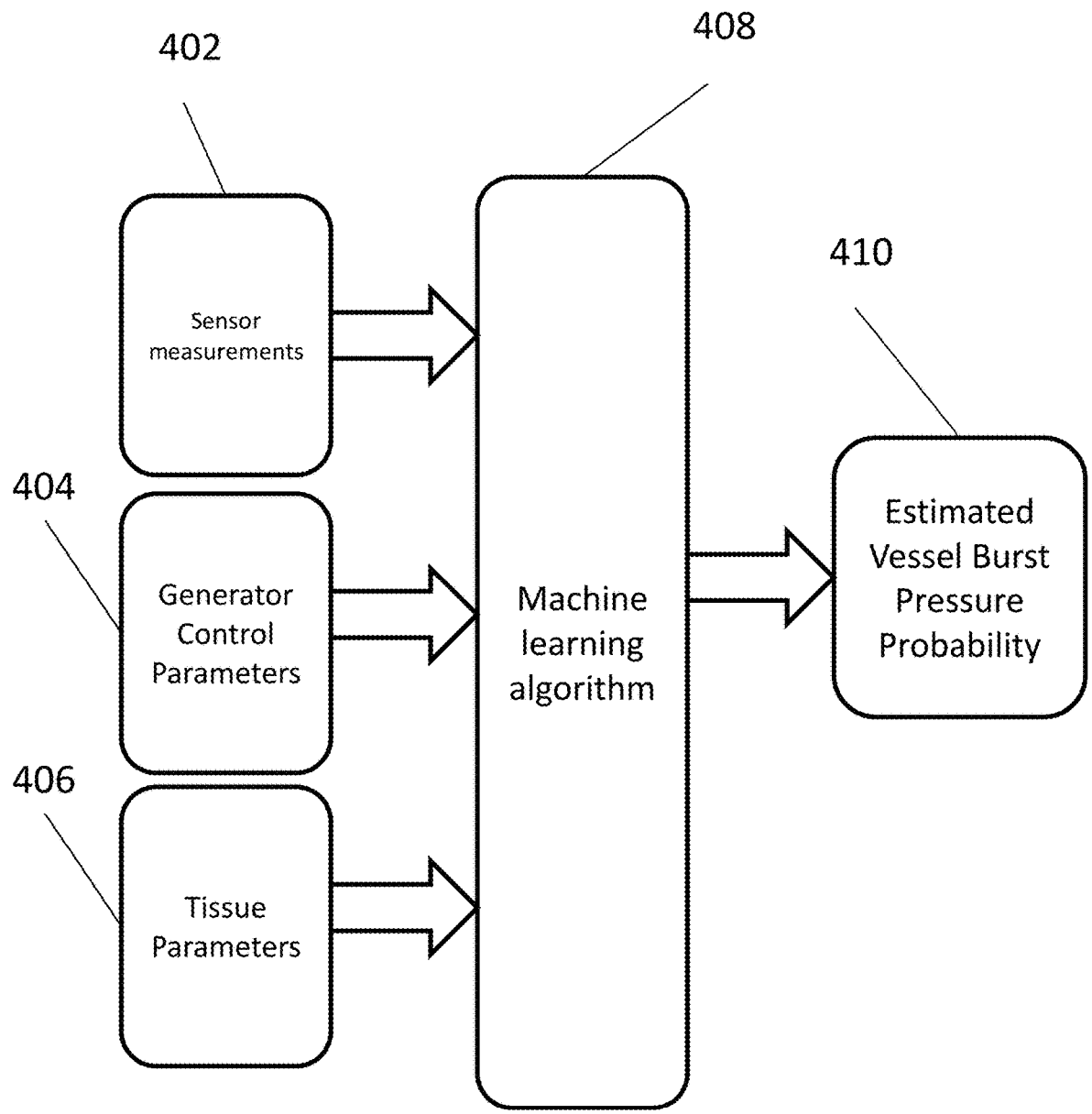
FIG. 4 is a logic diagram of a machine learning algorithm in accordance with the disclosure.

With reference to FIG. 4, a logic diagram of a machine learning algorithm 408 is shown in accordance with the disclosure. Training of the machine learning algorithm 408 may be based on sensor measurements 402, generator control parameters 404 and/or tissue parameters 406 as inputs to the machine learning algorithm 408, e.g., a neural network. The machine learning algorithm 408 outputs an estimation of burst pressure probability 410.

In various embodiments, the generator control parameters 404 that correlate with particular sensor measurements 402 are used as inputs to the machine learning algorithm 408 during training. In various embodiments, the generator control parameters 404 may include, for example, power, current, voltage, time, slopes of power, current, and/or voltage, or other generator 160 parameters. In various embodiments, the tissue parameters may include one or more of the following non-limiting list of impedance, tissue temperature, or accumulated energy. In various embodiments, the controller 500 may communicate to a remote server, for example, that stores adjusted control parameters, text data, and/or the output of the machine learning algorithm 408.

In various embodiments, the outputs of the machine learning algorithm 408, e.g., neural network, may be used as training data for reinforcement learning. It is contemplated that the training may be performed on a separate system, for example, GPU servers, simulation, etc., and the trained network would then be deployed in the surgical system. In various embodiments, the controller 500 outputs, from the machine learning algorithm 408, an estimated vessel burst pressure probability.

Figure 5:
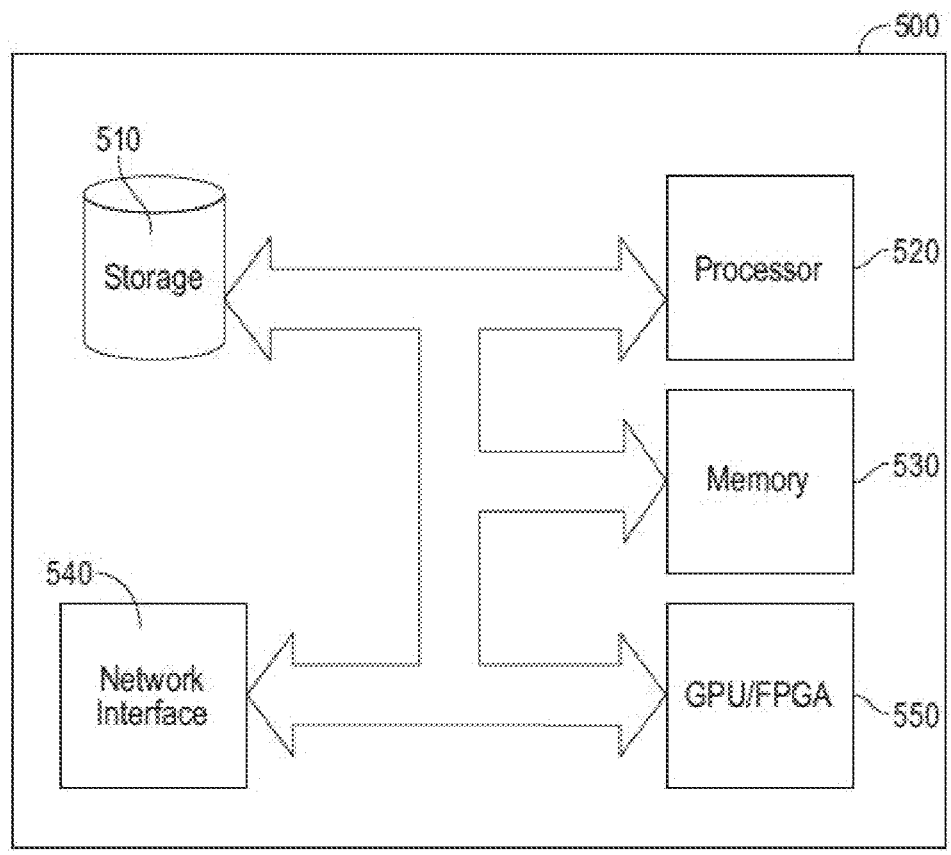
FIG. 5 is a block diagram of a controller provided in accordance with the disclosure and configured for use with the surgical system of FIG. 1A.

Referring to FIG. 5, the controller 500, in accordance with the disclosure, is shown. The controller 500 includes a processor 520 connected to a computer-readable storage medium or a memory 530 which may be a volatile type memory, e.g., RAM, or a non-volatile type memory, e.g., flash media, disk media, etc. In various embodiments, the processor 520 may be another type of processor such as, without limitation, a digital signal processor, a microprocessor, an ASIC, a graphics processing unit (GPU), field-programmable gate array (FPGA), or a central processing unit (CPU). In various embodiments, network inference may also be accomplished in systems that may have weights implemented as memistors, chemically, or other inference calculations, as opposed to processors.

In various embodiments, the memory 530 can be random access memory, read-only memory, magnetic disk memory, solid state memory, optical disc memory, and/or another type of memory. In various embodiments, the memory 530 can be separate from the controller 500 and can communicate with the processor 520 through communication buses of a circuit board and/or through communication cables such as serial ATA cables or other types of cables. The memory 530 includes computer-readable instructions that are executable by the processor 520 to operate the controller 500. In various embodiments, the controller 500 may include a network interface 540 to communicate with other computers or a server. In embodiments, a storage device 510 may be used for storing data. In various embodiments, the controller 500 may include one or more FPGAs 550. The FPGA 550 may be used for executing various machine learning algorithms such as those provided in accordance with the disclosure, as detailed below.

The memory 530 stores suitable instructions, to be executed by the processor 520, for receiving the sensed data, e.g., sensed data from sensor module 166 via ADCs 168 (see FIG. 2), accessing storage device 510 of the controller 500, determining one or more tissue parameters, e.g., burst pressure probability, based upon the sensed data and information stored in storage device 510, and providing feedback based upon the determined tissue parameters. Although illustrated as part of generator 160, it is also contemplated that controller 500 be remote from generator 160, e.g., on a remote server, and accessible by generator 160 via a wired or wireless connection. In embodiments where controller 500 is remote, it is contemplated that controller 500 may be accessible by and connected to multiple generators 160.

Storage device 510 of controller 500 stores one or more machine learning algorithms and/or models, configured to estimate one or more tissue parameters, e.g., burst pressure probability, based upon the sensed data received from sensory circuitry, e.g., from sensor module 166 via ADCs 168 (see FIG. 2). The machine learning algorithm(s) may be trained on and learn from experimental data and/or data from previous procedures initially input into the one or more machine learning applications in order to enable the machine learning application(s) to estimate the tissue parameters based upon such data. Such data may include tissue impedance data, power data, time, and/or any other suitable data.

Referring generally to FIGS. 2-5, machine learning algorithms are advantageous for use in determining vessel parameters at least in that complex sensor components, and pre-defined categorization rules and/or algorithms are not required. Rather, machine learning algorithms utilize the initially input data, e.g., the previous procedure data, current procedure data, and/or experimental data, to determine statistical features and/or correlations that enable the determination of vessel parameters of unknown vessels by analyzing data therefrom. Thus, with the one or more machine learning algorithms having been trained as detailed above, such can be used to determine parameters of vessel being sealed, e.g., using end effector assembly 10. More specifically, processor 520 of controller 500 is configured, in response to receiving sensed data from sensory circuitry, e.g., from sensor module 166 via ADCs 168, to input the sensed data into the machine learning algorithm(s) stored in storage device 510 in order to determine the one or more vessel parameters of the vessel being sealed using end effector assembly 10. Although described with respect to an electrosurgical system, the aspects and features of controller 500 and the machine learning algorithms configured for use therewith are equally applicable for use with other suitable surgical systems, e.g., an ablation system and/or an ultrasonic system.

Once the vessel parameters are determined by the controller 500, depending upon the vessel parameters, settings, user input, etc., controller 500 may for example, output an alert and/or warning to user interface, implement, switch, or modify a particular energy-delivery algorithm based upon which the power supply 164 and RF output stage 162 provide energy to end effector assembly 10, and/or inhibit further energy delivery to end effector assembly 10.

The terms "artificial intelligence," "data models," or "machine learning" may include, but are not limited to, neural networks, deep neural networks, recurrent neural networks (RNN), generative adversarial networks (GAN), Bayesian Regression, Naive Bayes, Monte Carlo Methods, nearest neighbors, least squares, means, and support vector regression, among other data science and artificial science techniques. Exemplary uses are identifying patterns and making predictions relating to vessel parameters, which will be described in more detail hereinbelow.

The term "application" may include a computer program designed to perform particular functions, tasks, or activities for the benefit of a user. Application may refer to, for example, software running locally or remotely, as a stand-alone program or in a web browser, or other software which would be understood by one skilled in the art to be an application. An application may run on the controller 500 or on a user device, including for example, on a mobile device, an IOT device, or a server system.

Figure 6:
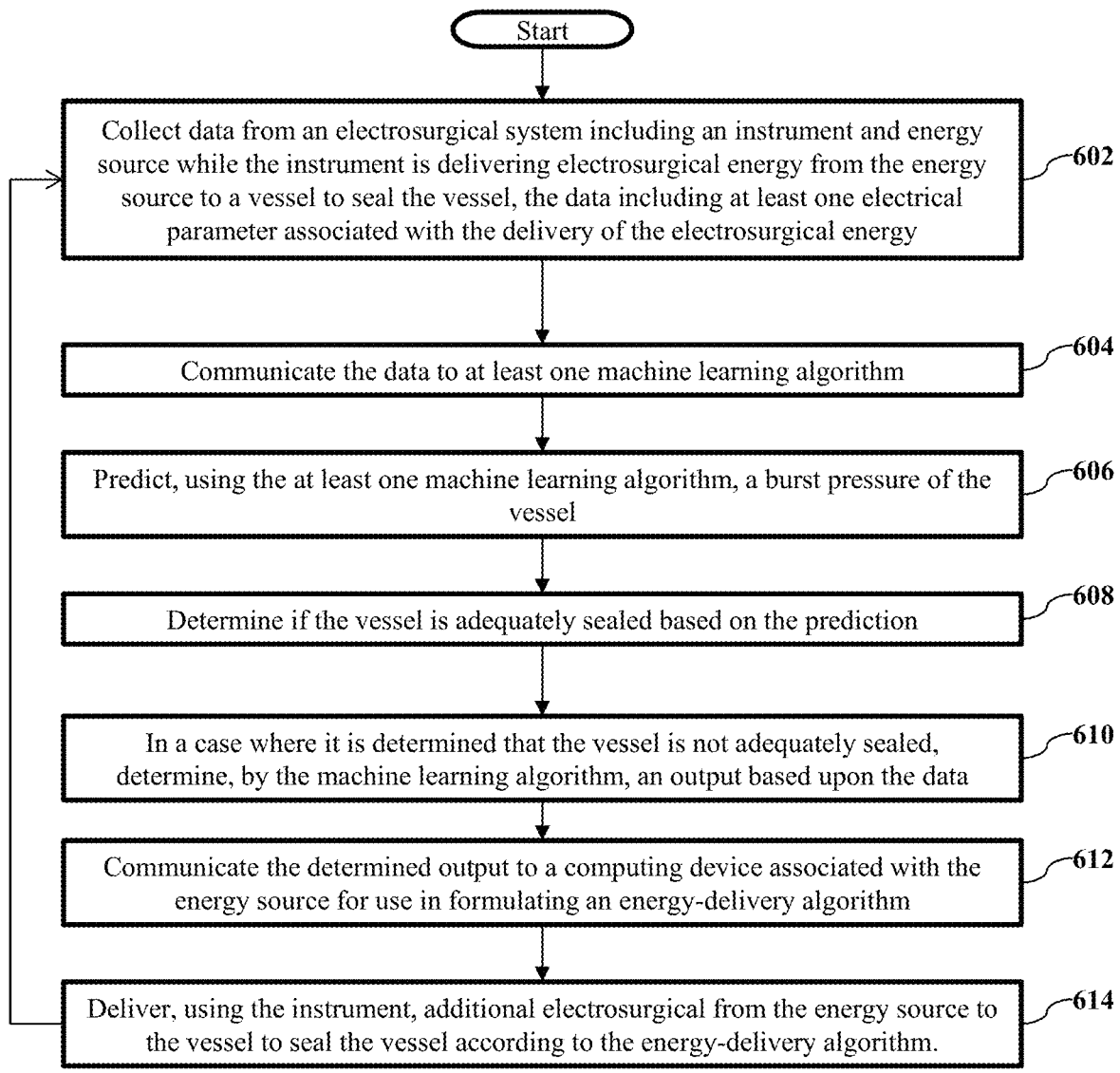
FIG. 6 is a flowchart of a method for controlling delivery of electrosurgical energy to a vessel to seal the vessel in accordance with the disclosure.

Referring now to FIG. 6, there is shown a flow diagram of a computer-implemented method 600 for controlling delivery of electrosurgical energy to a vessel to seal the vessel. Persons skilled in the art will appreciate that one or more operations of the method 600 may be performed in a different order, repeated, and/or omitted without departing from the scope of the disclosure. In various embodiments, the illustrated method 600 can operate in the controller 500 (FIG. 5), in a remote device, or in another server or system. In various embodiments, some or all of the operations in the illustrated method 600 can operate using an electrosurgical system, e.g., instrument 100 or 200 and the generator 160 (see FIGS. 1A and 1B). Other variations are contemplated to be within the scope of the disclosure. The operations of method 600 will be described with respect to a controller, e.g., controller 500 of generator 160 (FIGS. 2 and 5), but it will be understood that the illustrated operations are applicable to other systems and components thereof as well.

Initially, at step 602, the controller 500 may collect data, from an electrosurgical system including an instrument and energy source while the instrument is delivering electrosurgical energy from the energy source to a vessel to seal the vessel. The data may include at least one parameter associated with the delivery of the electrosurgical energy. For example, the data may include impedance, power, voltage, current, vessel temperature, vessel mass, vessel surface area, accumulated energy, or burst pressure probability.

For example, the electrosurgical system may include a generator and an electrosurgical instrument such as detailed above with respect to FIGS. 1A and 1B. While a surgeon is operating the electrosurgical system during surgery, they may use the system to apply electrosurgical (RF) energy to a vessel to seal the vessel. More specifically, with additional reference to FIG. 2, tissue 302 (e.g., a vessel) may be grasped between electrically conductive tissue treating surfaces 13, 14 of jaw members 11, 12 (or jaw members 21, 22 of FIG. 1B) and electrosurgical (RF) energy may be conducted between tissue treating surfaces 13, 14 and through tissue 302 to heat and thereby seal vessel 302. During such sealing process, the sensor circuitry, e.g., sensor module 166, of the generator 160 may sense parameters of the vessel and/or energy such as, for example, impedance and power, and/or may supply data from which impedance and/or power can be derived such as for example, time, voltage, and/or current data. It is contemplated that pressure may also be sensed or determined. This may occur as a snapshot or over a time interval and may be determined at the beginning of vessel sealing, e.g., at or within 250 ms of initiation of vessel sealing, to avoid permanent damage to tissue should it be determined that application of energy should be discontinued. The sensed data may include, for example, time that the power is applied for, power applied to the tissue, and/or impedance of the vessel. The sensor module 166 may measure data from the electrosurgical system, for example, the voltage and/or a current of the electrosurgical energy being delivered to the vessel. In various embodiments, the voltage and the current may be used to derive the power and/or the impedance. This sensed data obtained by the sensor circuitry may be relayed to the controller 500 (via the ADC's 168, in embodiments) for further processing, as detailed below.

In step 604, the controller 500 communicates the data as an input to a machine learning algorithm, e.g., a neural network. In embodiments, training the neural network may be accomplished by identifying patterns in the impedance curve shape and/or a power versus time curve. In various embodiments, a neural network may be used for training data, for example: impedance, power, time, tissue electrical properties, tissue thermal properties, electrosurgical device electrical properties, or electrosurgical device thermal properties of the jaw members 11, 12 (FIG. 1A) or jaw members 21, 22 (FIG. 1B), may be used as input data. In various embodiments, the outputs of the neural network may be used as training data for supervised learning. It is contemplated that the training may be performed on a separate system, for example, GPU servers, simulation, etc., and the trained network would then be deployed in the electrosurgical system 1100.

In step 606, the controller 500 estimates a burst pressure probability of the sealed vessel using the machine learning algorithm. For example, once a vessel is sealed, burst pressure probability is a metric of the likelihood that the vessel will not burst upon application of a fluid pressure below a threshold pressure. For example, a target burst pressure probability for determining an adequately sealed vessel may be a 95% probability of a burst pressure greater than 360 mmHg, although other suitable probabilities and/or pressures (twice, thrice, etc. systolic blood pressure) are also contemplated. In various embodiments, using the machine learning algorithm, burst pressure probability may be estimated. Burst pressure probability indicates the likelihood of when the sealed vessel will fail and, thus, is a metric of the adequacy of the seal. That is, by estimating burst pressure probability, the controller 500 may determine whether the vessel is sealed adequately or, if not, that energy needs to continue to be applied until the burst pressure probability is reached.

In various embodiments, the neural network may include a feed-forward network, a convolutional network, or a recurrent network. In various embodiments, the neural network may be trained using one or more of measuring sensor data or identifying patterns in data. In various embodiments, training the machine learning algorithm may be performed by a computing device outside of the generator 160, and the resulting algorithm may be communicated to the controller 500 of generator 160.

In various embodiments, the neural network may be trained using training data, which includes, for example, impedance, tissue temperature, tissue mass, tissue surface area, accumulated energy, or burst pressure probability. In various embodiments, training may include at least one of supervised learning, unsupervised learning or reinforcement learning.

Reinforcement learning is an area of machine learning concerned with how software agents ought to take actions in an environment so as to maximize some notion of cumulative reward. For example, the following illustrative example may be useful for understanding the basic methodology behind reinforcement learning: First, an agent may observe and construct their own representation of an environment (state). Next, the agent will take certain actions and observe the response received given in the environment (updated state). If the response received by the agent from the action taken in a given environment is not desired, then the agent may receive a negative reward, and, subsequently, may be less likely to take that particular action again in that given state. If the response received by the agent from the action taken in a given environment is desired, then the agent will receive a positive reward, and subsequently will be more likely to take that particular action again in that given state. This process is repeated until the agent finds a policy (what actions to take under different circumstances) that maximizes the total cumulative rewards.

In various embodiments, the neural network may include, for example, a two-layer feedforward network. In various embodiments, the neural network may include a feedforward network, a convolutional network, and/or a recurrent network.

At step 608, the controller 500 determines if the vessel is adequately sealed based on the estimated burst pressure probability. At step 610, in a case where the controller 500 determines that the vessel is not adequately sealed, the machine learning algorithm, outputs and indication of such, either as an estimation of the burst pressure probability itself, a relative metric of the disparity between the estimated burst pressure probability and the target burst pressure probability, or in some other manner.

At step 612 the controller 500 communicates the indication that was output from the machine learning algorithm to a computing device associated with the energy source, e.g., of controller 500, for use in formulating, e.g., switching, confirming, modifying, generating, etc., a vessel sealing algorithm.

At step 614, the instrument delivers additional electrosurgical from the energy source to the vessel to seal the vessel in accordance with the vessel sealing algorithm. When it is determined that the vessel is adequately sealed (e.g., after one or more iterations of the above, an indication of the same is output from the machine learning algorithm and communicated by the controller 500 to the computing device to, e.g., cease the supply of energy and end the vessel sealing process.

Figure 7:
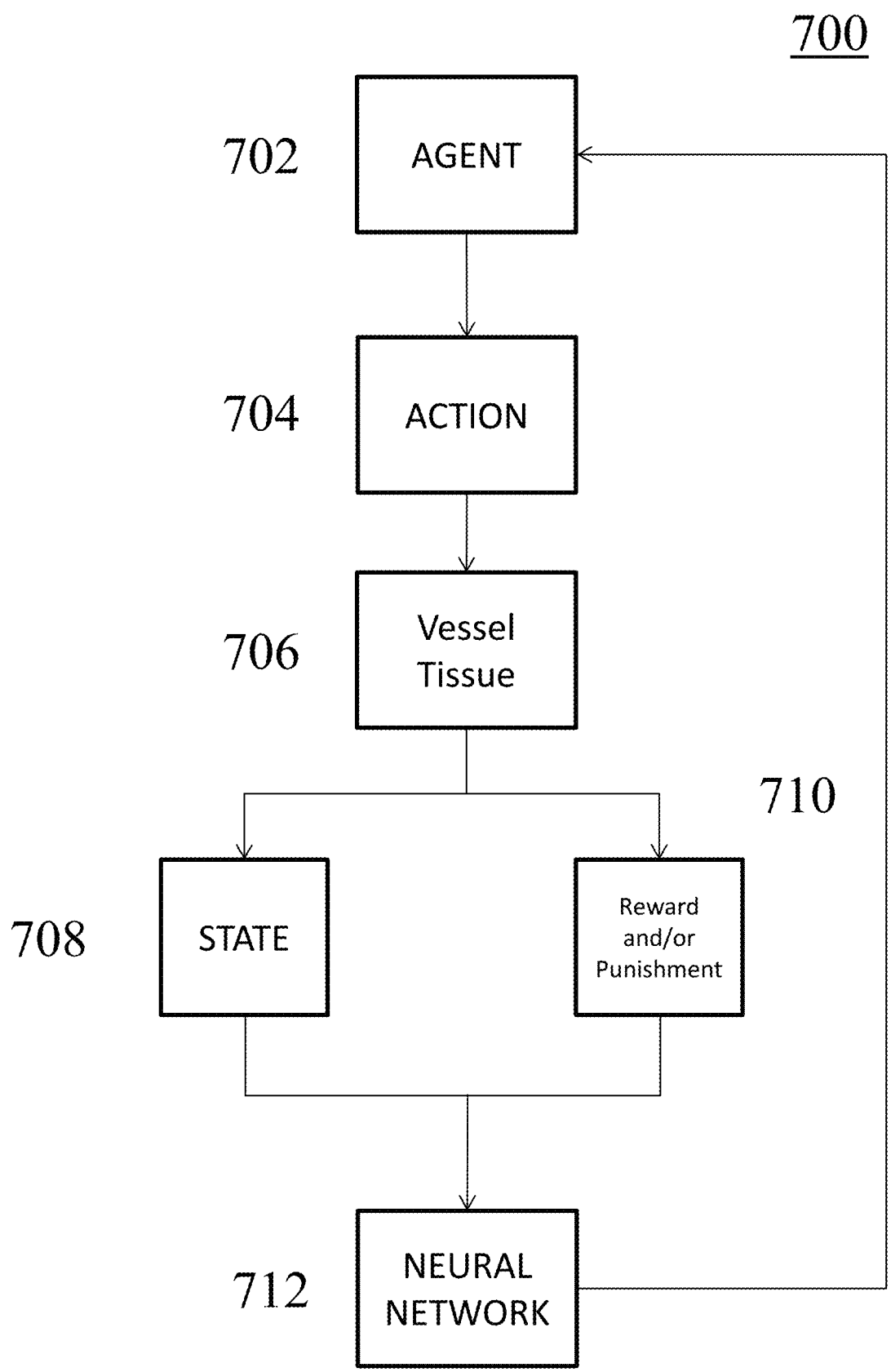
FIG. 7 is a block diagram of reinforcement learning provided in accordance with the disclosure.

With reference to FIG. 7, a block diagram of reinforcement training in accordance with the disclosure is shown. As previously described hereinabove, reinforcement learning is an area of machine learning concerned with how software agents ought to take actions in an environment so as to maximize some notion of cumulative reward. Initially, when sealing a vessel, power may be applied to the vessel 706 via an electrosurgical instrument. Next, an agent 702 may observe and construct their own representation of the vessel 706 based on the vessel parameters (state 708), such as accumulated energy, impedance, or temperature. Next, the agent 702 will take certain actions 704 (e.g., applying energy, cease applying energy, changing the application of energy) and observe the response received given the environment (e.g., the estimated burst pressure probability). The controller 500 may determine rewards and/or punishments 710 used to train the neural network 712 in reinforcement learning 700.

The reward may include a value based on burst pressure probability, and the punishment may include a value based on an impedance being lower than a threshold value. The reward, more specifically, may include a burst pressure probability value of between 0 and 1. In various embodiments, the burst pressure probability value may include, in a case that the vessel temperature is a first temperature range (e.g., 70 C-80 C) for a first predetermined period of time (e.g., 100 mS) for protein denaturing, an increase in the burst pressure probability value of, for example, about 0.33.

In various embodiments, in a case that the vessel temperature is a second temperature range (e.g., between 140 C-152 C) for a second predetermined period of time for a percentage of water to be removed (e.g., 25%), the burst pressure probability value may be increased by, for example, about 0.33. In various embodiments, in a case that the vessel temperature is a third temperature range (e.g., 40 C-50 C) for a third predetermined period of time (e.g., 100 mS) for allowing thermoset gelatin to congeal and the jaw members to cool, the burst pressure probability value may be increased by about 0.33.

In various embodiments, an impedance punishment value may be between −1 and 0. In various embodiments, the impedance punishment value may be set, in a case that impedance of the vessel is greater than a first impedance threshold (e.g., 4000 ohms), to −1. In various embodiments, in a case where the impedance of the vessel is less than a first impedance value threshold (e.g., 4000 ohms), the impedance punishment value may be set to 0.

In various embodiments, the neural network 712 may determine an action 704 based on the reward and punishment 710. For example, the action may include increasing or decreasing the power applied to a vessel to seal the vessel. In various embodiments, the controller 500 may determine that the vessel is adequately sealed, and the action 704 may include ceasing delivery of the electrosurgical energy or the additional electrosurgical energy. It is contemplated that the punishment may include the vessel temperature being above a predetermined threshold, the voltage being above a predetermined threshold, and/or the detection of arcing.

Figure 8:
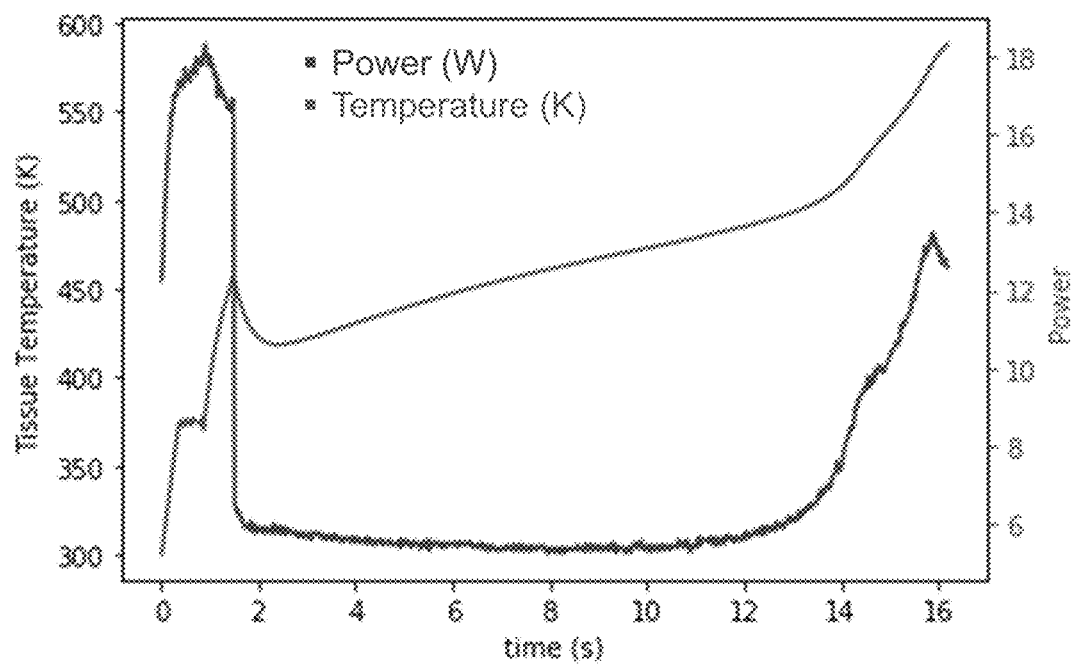
FIG. 8 is a graph of energy-tissue interaction provided in accordance with the disclosure.

With reference to FIG. 8, a graph is shown illustrating energy-tissue interaction in accordance with the disclosure. In various embodiments, as energy is applied to the tissue (e.g., a vessel) for sealing, the temperature of the tissue may increase.

Figure 9A:
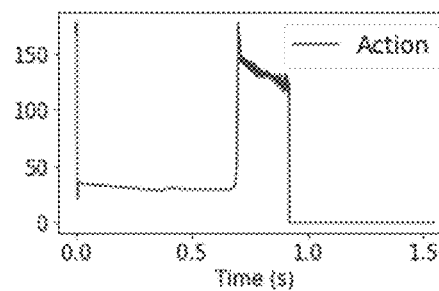
FIGS. 9A-9F are various graphs illustrating energy-tissue interaction provided in accordance with the disclosure.
Figure 9D:
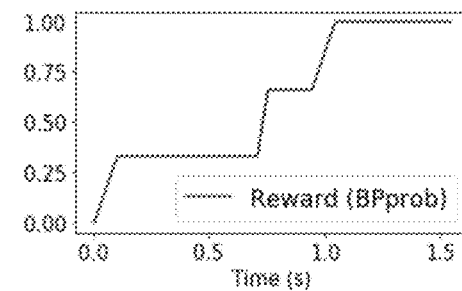
Figure 9B:
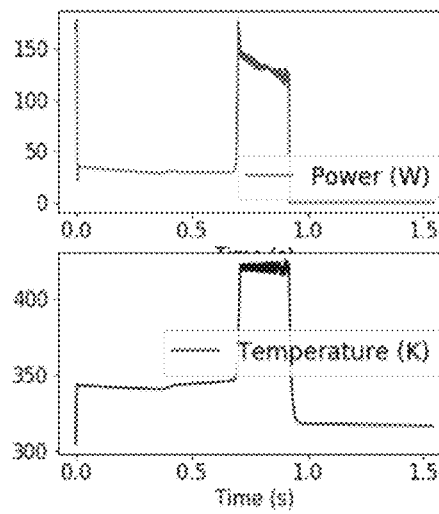
Figure 9E:
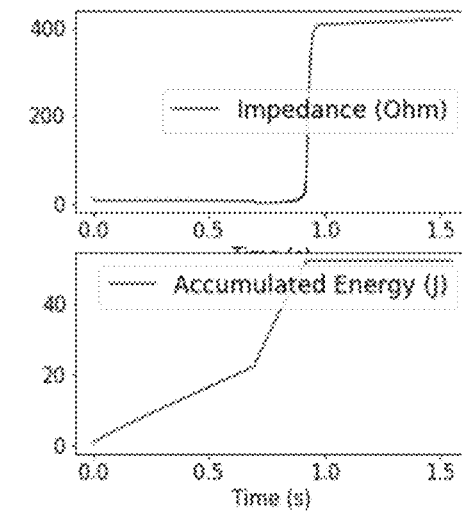
Figure 9C:
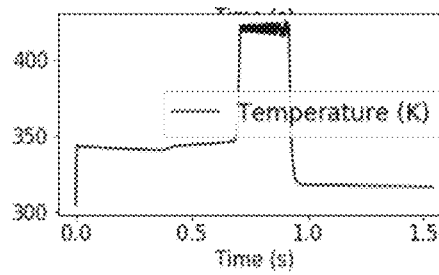
Figure 9F:
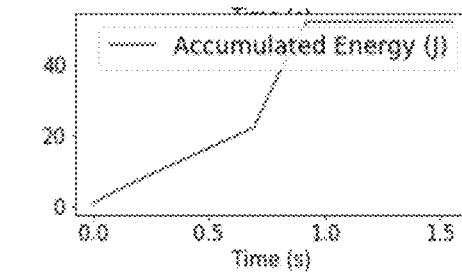

With reference to FIGS. 9A-F, various graphs are shown illustrating energy-tissue interaction in accordance with the disclosure. In various embodiments, power may be applied to the vessel over time, as shown in FIG. 9B. In various embodiments, the action FIG. 9A may be the power being applied to tissue (e.g., a vessel) to seal the vessel. In various embodiments, as shown in FIG. 9C as the power is applied to the vessel over time, the temperature of the vessel may increase or decrease based on the applied power. As power is applied to the vessel over time, the probability of burst pressure may increase, as shown in FIG. 9D. After sealing is complete, the impedance (ohms) of the vessel may increase, as shown in FIG. 9E. For example, impedance may increase from a low impedance to approximately 400 ohms as moisture is removed during the sealing process. In various embodiments, as shown in FIG. 9F as energy is applied to the vessel over time, the accumulated energy (J) may increase.

Figure 10:
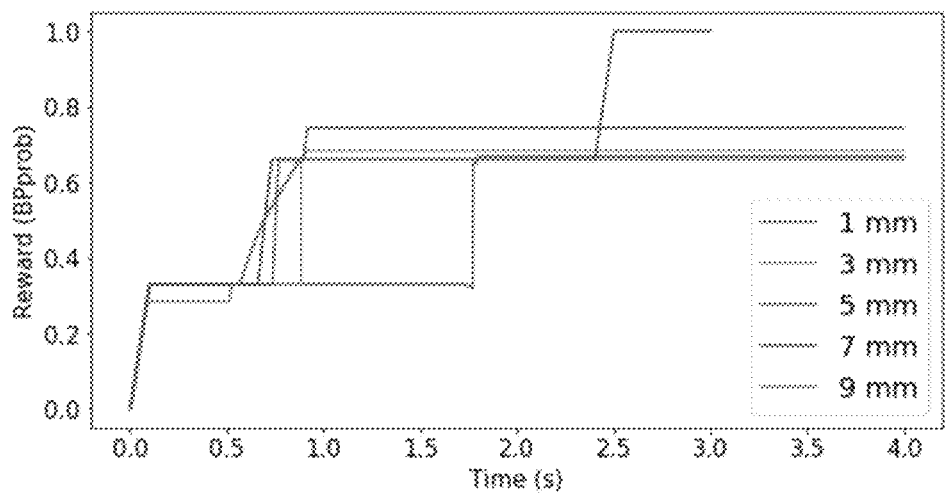
FIG. 10 is a graph of burst pressure probability vs. time for various vessel diameters provided in accordance with the disclosure.
Figure 11:
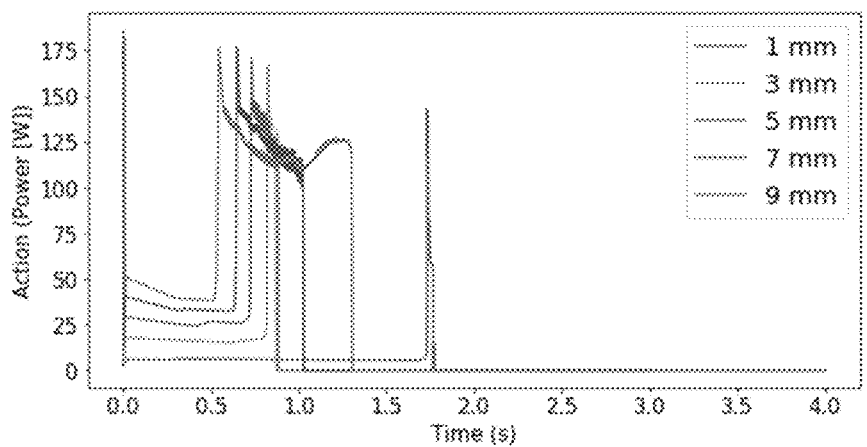
FIG. 11 is a graph of power vs. time for various vessel diameters provided in accordance with the disclosure.
Figure 12:
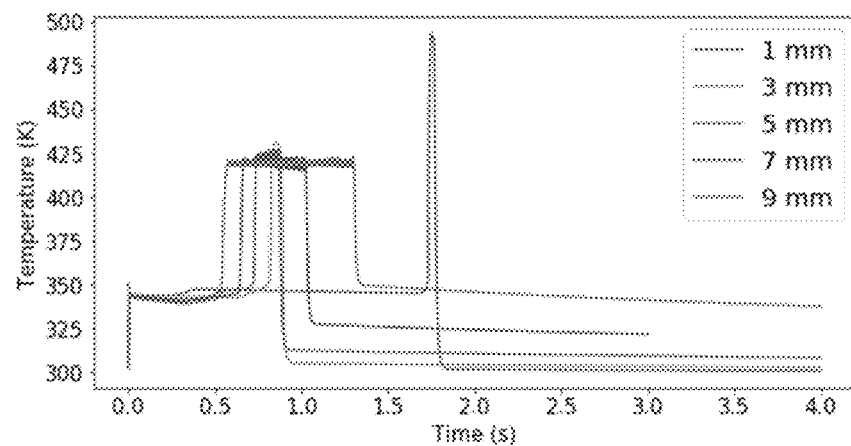
FIG. 12 is a graph of tissue temperature vs. time for various vessel diameters provided in accordance with the disclosure.
Figure 13:
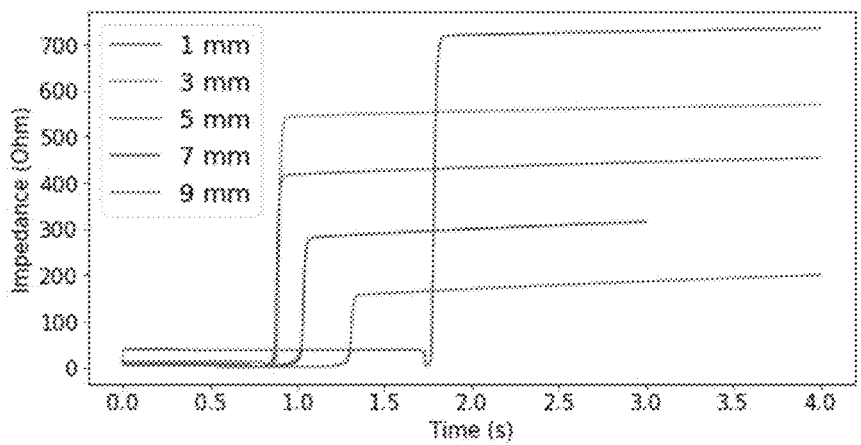
FIG. 13 is a graph of tissue impedance vs. time for various vessel diameters provided in accordance with the disclosure.
Figure 14:
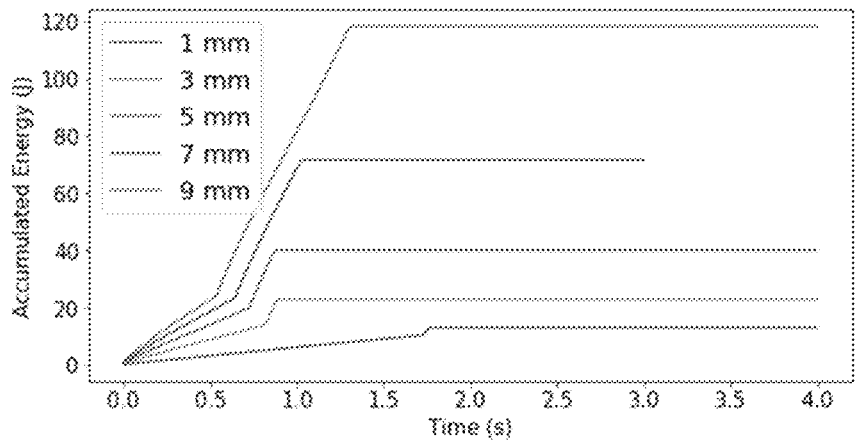
FIG. 14 is a graph of accumulated energy vs. time for various vessel diameters provided in accordance with the disclosure.

With reference to FIGS. 10-14 graphs of various parameters are shown for various vessel diameters during vessel sealing using the machine learning algorithm in accordance with the disclosure. FIG. 10 shows a diagram of burst pressure probability vs. time for various vessel diameters (e.g., 1 mm, 3 mm, 5 mm, 7 mm, and 9 mm). For example, as energy is applied to the vessel over time, the probability that a vessel will not burst below a threshold value may increase, and/or the threshold value itself may increase. FIG. 11 shows a diagram of action vs. time for various vessel diameters. For example, the action may include the power being applied to the vessel over time. Different diameter vessels may require a different amount of power for an adequate seal. FIG. 12 shows a diagram of vessel temperature vs. time for various vessel diameters. For example, for different diameter vessels, as power is applied over time during the course of a seal, the vessel temperature may change differently for each diameter vessel. FIG. 13 shows a diagram of vessel impedance vs. time for various vessel diameters. For example, for different diameter vessels, as power is applied over time during the course of a seal, the vessel impedance may change differently for each diameter vessel. FIG. 14 shows a diagram of accumulated energy vs. time for various vessel diameters. Accumulated energy is the amount of energy applied to the vessel over time, (i.e., $\int$power dt).

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A computer-implemented method for controlling delivery of electrosurgical energy to a vessel to seal the vessel, the computer-implemented method comprising:
  collecting data from an electrosurgical system including an instrument and energy source while the instrument is delivering electrosurgical energy from the energy source to a vessel to seal the vessel, the data including at least one electrical parameter associated with the delivery of the electrosurgical energy;

communicating the data to a first neural network;
predicting, by the first neural network, a burst pressure probability of the vessel, based on:
constructing a representation of the vessel based on vessel parameters including accumulated energy, impedance, and temperature;
performing an action including at least one of applying energy, ceasing application of energy, or changing application of energy;
receiving, as a response, further data collected after the action is performed;
predicting a burst pressure probability value based on the response;
determining a reward or a punishment, wherein the reward is based on the burst pressure probability and the punishment is based on an impedance being lower than a threshold value; and
training the first neural network based on the reward or punishment; and
determining if the vessel is adequately sealed based on the prediction;
in a case where it is determined that the vessel is not adequately sealed:
determining, by a second neural network, an output based upon the data, wherein the second neural network is different than the first neural network;
communicating the determined output to a computing device associated with the energy source for use in formulating an energy-delivery algorithm; and
delivering, using the instrument, additional electrosurgical energy from the energy source to the vessel to seal the vessel according to the energy-delivery algorithm.

2. The method of claim 1, wherein at least one of the first neural network or the second neural network includes at least one of a feed-forward network, a convolutional network, or a recurrent network.

3. The method of claim 1, the method further includes training at least one of the first neural network or the second neural network based on one or more of measuring sensor data or identifying patterns in data.

4. The method of claim 1, the method further includes training at least one of the first neural network or the second neural network based on training data including at least one of: impedance, vessel temperature, vessel mass, vessel surface area, accumulated energy, or burst pressure probability.

5. The method of claim 4, wherein the training includes at least one of supervised learning, unsupervised learning or reinforcement learning.

6. The method of claim 1, wherein the burst pressure probability value is a scaler and determined by:
in a case that the vessel temperature is a first temperature range for a first predetermined period of time for protein denaturing, increasing the burst pressure probability value by a first amount;
in a case that the vessel temperature is a second temperature range for a second predetermined period of time for a predetermined percentage of water to be removed, increasing the burst pressure probability value by a second amount; and
in a case that the vessel temperature is a third temperature range for a third predetermined period of time for allowing a thermoset gelatin to congeal and jaws to cool, increasing the burst pressure probability value by a third amount.

7. The method of claim 6, wherein the impedance punishment value is a second scaler and determined by:

in a case that impedance of the vessel is greater than a first impedance threshold, setting the impedance punishment value to −1; and
in a case where the impedance of the vessel is less than the first impedance threshold, setting the impedance punishment value to 0.

8. The method of claim 1, further comprising, in a case where it is determined that the vessel is adequately sealed, ceasing delivery of the electrosurgical energy or the additional electrosurgical energy.

9. A system for controlling electrosurgical energy, the system comprising:
an electrosurgical system including an instrument and energy source;
one or more processors; and
at least one memory coupled to the one or more processors, the at least one memory having instructions stored thereon which, when executed by the one or more processors, cause the system to:
collect data from the electrosurgical system while the instrument is delivering electrosurgical energy from the energy source to a vessel to seal the vessel, the data including at least one electrical parameter associated with the delivery of the electrosurgical energy;
communicate the data to a first neural network;
predict, by the first neural network, a burst pressure probability of the vessel, based on:
constructing a representation of the vessel based on vessel parameters including accumulated energy, impedance, and temperature;
performing an action including at least one of applying energy, ceasing application of energy, or changing application of energy;
receiving, as a response, further data collected after the action is performed;
predicting a burst pressure value probability based on the response;
determining a reward or a punishment, wherein the reward is based on the burst pressure probability and the punishment is based on an impedance being lower than a threshold value; and
training the first neural network based on the reward or punishment; and
determine if the vessel is adequately sealed based on the prediction;
in a case where it is determined that the vessel is not adequately sealed:
determine, by a second neural network, an output based upon the data, wherein the second neural network is different than the first neural network;
communicate the determined output to a computing device associated with the energy source for use in formulating an energy-delivery algorithm; and
deliver, using the instrument, additional electrosurgical energy from the energy source to the vessel to seal the vessel according to the energy-delivery algorithm.

10. The system of claim 9, wherein at least one of the first neural network or the second neural network includes at least one of a feed-forward network, a convolutional network, or a recurrent network.

11. The system of claim 10, wherein the instructions, when executed, further cause the system to train the second neural network based on one or more of measuring sensor data or identifying patterns in data.

12. The system of claim 11, wherein the instructions, when executed, further cause the system to train the at least one of the first neural network or the second neural network based on training data including at least one of: impedance, vessel temperature, vessel mass, vessel surface area, accumulated energy, or burst pressure probability.

13. The system of claim 12, wherein the training includes at least one of supervised learning, unsupervised learning or reinforcement learning.

14. The system of claim 9, wherein the burst pressure probability value is between 0 and 1 and determined by:
   in a case that the vessel temperature is a first temperature range for a first predetermined period of time for protein denaturing, increasing the burst pressure probability value by a first amount;
   in a case that the vessel temperature is a second temperature range for a second predetermined period of time for a predetermined percentage of water to be removed, increasing the burst pressure probability value by a second amount; and
   in a case that the vessel temperature is a third temperature range for a third predetermined period of time for allowing a thermoset gelatin to congeal and jaws to cool, increasing the burst pressure probability value by a third amount; and
   the impedance punishment value is between −1 and 0 and determined by:
      in a case that impedance of the vessel is greater than a first impedance threshold, setting the impedance punishment value to −1; and
      in a case where the impedance of the vessel is less than the first impedance threshold, setting the impedance punishment value to 0.

15. The system of claim 9, wherein in a case where it is determined that the vessel is adequately sealed, the instructions, when executed, further cause the system to cease delivery of the electrosurgical energy or the additional electrosurgical energy.

16. A non-transitory storage medium that stores a program causing a computer to execute a computer-implemented method for controlling delivery of electrosurgical energy to a vessel to seal the vessel, the computer-implemented method comprising:
   collecting data from an electrosurgical system including an instrument and energy source while the instrument is delivering electrosurgical energy from the energy source to a vessel to seal the vessel, the data including at least one electrical parameter associated with the delivery of the electrosurgical energy;
   communicating the data to a first neural network;
   predicting, by the first neural network, a burst pressure probability of the vessel, based on:
      constructing a representation of the vessel based on vessel parameters including accumulated energy, impedance, and temperature;
      performing an action including at least one of applying energy, ceasing application of energy, or changing application of energy;
      receiving, as a response, further data collected after the action is performed;
      predicting the burst pressure probability based on the response;
      determining a reward or a punishment, wherein the reward is based on the burst pressure probability and the punishment is based on an impedance being lower than a threshold value; and
      training the first neural network based on the reward or punishment; and
   determining if the vessel is adequately sealed based on the prediction; in a case where it is determined that the vessel is not adequately sealed:
   determining, by a second neural network, an output based upon the data, wherein the second neural network is different than the first neural network;
   communicating the determined output to a computing device associated with the energy source for use in formulating an energy-delivery algorithm; and
   delivering, using the instrument, additional electrosurgical from the energy source to the vessel to seal the vessel according to the energy-delivery algorithm.

* * * * *